(12) United States Patent
Akers

(10) Patent No.: US 7,630,469 B2
(45) Date of Patent: *****Dec. 8, 2009

(54) METHOD FOR ON-LINE EVALUATION OF MATERIALS USING PROMPT GAMMA RAY ANALYSIS

(75) Inventor: Douglas W. Akers, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 968 days.

This patent is subject to a terminal disclaimer.

(21) Appl. No.: 10/788,743

(22) Filed: Feb. 25, 2004

(65) Prior Publication Data

US 2005/0117682 A1 Jun. 2, 2005

Related U.S. Application Data

(63) Continuation-in-part of application No. 10/383,096, filed on Mar. 5, 2003, which is a continuation-in-part of application No. 09/932,531, filed on Aug. 17, 2001, now Pat. No. 7,231,011.

(51) Int. Cl.
*G21G 1/12* (2006.01)
(52) U.S. Cl. ............... 376/157; 376/159; 250/358.1
(58) Field of Classification Search ............... 376/157, 376/158, 159; 250/358.1, 308
See application file for complete search history.

(56) References Cited

U.S. PATENT DOCUMENTS

| | | |
|---|---|---|
| 2,509,344 A | 5/1950 | Herzog |
| 2,811,650 A | 10/1957 | Wagner |
| 3,593,025 A | 7/1971 | Grosskreutz |
| 3,792,253 A | 2/1974 | Wylie et al. |
| 3,803,416 A | 4/1974 | Strauss |
| 3,924,125 A | 12/1975 | Murray |
| 3,970,855 A | 7/1976 | Holt et al. |
| 4,064,438 A | 12/1977 | Alex et al. |
| 4,463,263 A | 7/1984 | Padawer |
| 4,622,200 A | 11/1986 | Gold et al. |
| 4,756,866 A | 7/1988 | Alvarez |

(Continued)

OTHER PUBLICATIONS

Derlet et al., A positron annihilation lifetime spectroscopy study of porous silicon using a continuous lifetime fitting algorithm, Journal of Materials Science Letters 15 (1996), pp. 1949-1952.*

(Continued)

*Primary Examiner*—Rick Palabrica
(74) *Attorney, Agent, or Firm*—Fennemore Craig, P.C.

(57) ABSTRACT

A method for evaluating a material specimen comprises: Mounting a neutron source and a detector adjacent the material specimen; bombarding the material specimen with neutrons from the neutron source to create prompt gamma rays within the material specimen, some of the prompt gamma rays being emitted from the material specimen, some of the prompt gamma rays resulting in the formation of positrons within the material specimen by pair production; collecting positron annihilation data by detecting with the detector at least one emitted annihilation gamma ray resulting from the annihilation of a positron; storing the positron annihilation data on a data storage system for later retrieval and processing; and continuing to collect and store positron annihilation data, the continued collected and stored positron annihilation data being indicative of an accumulation of lattice damage over time.

21 Claims, 7 Drawing Sheets

U.S. PATENT DOCUMENTS

| | | | |
|---|---|---|---|
| 4,835,390 | A | 5/1989 | Blatchley et al. |
| 4,897,549 | A | 1/1990 | Zerda et al. |
| 4,980,901 | A | 12/1990 | Miller |
| 4,983,841 | A | 1/1991 | Stewart et al. |
| 5,175,756 | A | 12/1992 | Pongrantz et al. |
| 5,200,619 | A | 4/1993 | Kumar et al. |
| 5,530,245 | A | 6/1996 | Huang |
| 5,774,520 | A | 6/1998 | Bolotin |
| 6,178,218 | B1 | 1/2001 | Akers |
| 6,236,050 | B1 | 5/2001 | Tumer |
| 6,639,210 | B2 | 10/2003 | Odom et al. |
| 6,693,277 | B2 | 2/2004 | Cowan et al. |
| 2003/0165213 | A1 | 9/2003 | Maglich et al. |

OTHER PUBLICATIONS

Banzuch et al., "Study of the Van Cittert and Gold iterative methods of deconvolution and their application in the deconvolution of experimental spectra of positron annihilation," Nuclear Instruments and Methods in Physics Research A 384 (1997), pp. 506-516.*

Zhu et al., "Analysis of positron annihilation lifetime data presented as a sum of convoluted exponentials with the program SPLMOD", Nuclear Instruments and Methods in Physics Research A284 (1989), pp. 443-451.*

Shaffer, Deconvoluted Doppler Broadened Positron Annihilation Spectroscopy: Characterization of Defects in Aluminum, University Microfilms International, 1985.*

Gregory et al., "Analysis of Positron Annihilation Lifetime Data by Numerical Laplace Innversion with Program CONTIN," Nuclear Instruments and Methods in Physics Research A290 (1990), pp. 172-182.*

Richard B. Firestone, "The Berkeley Laboratory Isotopes Project Exploring the Table of Isotopes" (http://is.lbl.gov/education/isotopes.htm) last updated May 22, 2000, accessed by Examiner on Nov. 10, 2003, 8:51 am.

* cited by examiner

US 7,630,469 B2

METHOD FOR ON-LINE EVALUATION OF MATERIALS USING PROMPT GAMMA RAY ANALYSIS

CROSS-REFERENCE TO RELATED APPLICATION

This is a continuation-in-part of co-pending U.S. patent application Ser. No. 10/383,096, filed on Mar. 5, 2003, which is a continuation-in-part of co-pending U.S. patent application Ser. No. 09/932,531, filed on Aug. 17, 2001, now U.S. Pat. No. 7,231,011 both of which are hereby incorporated herein by reference for all that they disclose.

GOVERNMENT RIGHTS

The United States Government has rights in the following invention pursuant to Contract No. DE-AC07-99ID13727 between the U.S. Department of Energy and Bechtel BWXT Idaho, LLC.

FIELD OF INVENTION

This invention relates generally to the testing and evaluation of materials and more specifically to methods and apparatus for performing non-destructive testing of materials using position annihilation.

BACKGROUND

Non-destructive material evaluation refers to any of a wide variety of techniques that may be utilized to examine materials for defects and/or evaluate the materials without requiring that the materials first be destroyed. Such non-destructive material evaluation is advantageous in that all materials or products may be tested for defects. After being evaluated, acceptable (e.g., substantially defect-free or with acceptable defect levels) materials may be placed in service, while the defective materials may be re-worked or scrapped, as may be required. Non-destructive evaluation techniques are also advantageous in that materials already in service may be evaluated or examined in-situ, thereby allowing for the early identification of materials or components that may be subject to in-service failure. The ability to evaluate or examine new or in-service materials has made non-destructive material evaluation techniques of great importance in safety- or failure-sensitive technologies, such as, for example, in conventional aviation and space technologies, as well as in nuclear systems and in power generation systems.

One type of non-destructive evaluation technique, generally referred to as positron annihilation, is particularly promising in that it is theoretically capable of detecting fatigue and other types of damage in metals at its earliest stages. While several different positron annihilation techniques exist, as will be described below, all involve the detection of positron annihilation events in order to ascertain certain information about the material or object being tested.

By way of background, complete annihilation of a positron and an electron occurs when both particles collide and their combined mass is converted into energy in the form of two (and occasionally three) photons (e.g., gamma rays). If the positron and the electron are both at rest at the time of annihilation, the two gamma rays are emitted in exactly opposite directions (e.g., 180° apart) in order to satisfy the requirement that momentum be conserved. Each annihilation gamma ray has an energy of about 511 keV, the rest energies of an electron and a positron.

In positron annihilation analysis, the momentum of the positron is related to the environment in which it resides. For example, positron momentum is relatively low in defects (e.g., microcracks in composite materials and polymers) or in large lattice structures, whereas positron momentum is higher in defect-free or tight lattice structures. One way to determine the momentum of the positron is to measure the degree of broadening of the gamma energy line caused by the annihilation event. Alternatively, the momentum of the positron may be derived from the deviation from 180° of the annihilation gamma rays.

Additional information about the electron density of the material at the site of annihilation may be obtained by determining the average lifetime of the positrons before they are annihilated. Still other information about the annihilation event may be detected and used to derive additional or supplemental information regarding the material being tested, such as the presence of contaminants or pores. Accordingly, the detection of positrons and the products of annihilation events provide much information relating to defects and other characteristics of the material or object being tested.

As mentioned above, several different positron annihilation techniques have been developed. In one type of positron annihilation technique, positrons from a radioactive source (e.g., $^{22}$Na, $^{68}$Ge, or $^{58}$Co) are directed toward the material to be tested. Upon reaching the material, the positrons are rapidly slowed or "thermalized." That is, the positrons rapidly loose most of their kinetic energy by collisions with ions and free electrons present at or near the surface of the material. After being thermalized, the positrons then annihilate with electrons in the material. During the diffusion process, the positrons are repelled by positively-charged nuclei, thus tend to migrate toward defects such as dislocations in the lattice sites where the distances to positively-charged nuclei are greater. In principle, positrons may be trapped at any type of lattice defect having an attractive electronic potential. Most such lattice defects are so-called "open-volume" defects and include, without limitation, vacancies, vacancy clusters, vacancy-impurity complexes, dislocations, grain boundaries, voids, and interfaces. In composite materials or polymers, such open-volume defects may be pores or microcracks.

Generally speaking, positron annihilation techniques utilizing external positron sources are of limited utility in that the positrons from the external positron sources cannot penetrate very deeply into the materials. As a result, such techniques are limited to evaluating the surface structures of the materials being tested.

Another type of positron annihilation technique replaces the external positron source with an external neutron source. Neutrons from the neutron source are directed toward the material being tested. Given sufficient energies, the neutrons will, in certain materials, result in the formation of isotopes that produce positrons. Such isotopes are commonly referred to as positron emitters, and include certain isotopes of copper, cobalt, and zinc. The positrons produced within the materials by the positron emitters then migrate to lattice defect sites, ultimately annihilating with electrons to produce gamma rays. This type of positron annihilation technique is often referred to as "neutron-activated positron annihilation" because it utilizes neutrons to trigger or induce the production of positrons.

Neutron-activated positron annihilation techniques are advantageous over techniques that utilize external positron sources because the neutrons from the external neutron sources penetrate more deeply into the materials being tested than do positrons alone (e.g., from the external positron sources). Therefore, neutron-activated positron annihilation systems are generally capable of detecting flaws deep within the material rather than merely on the surface. Disadvantageously, however, neutron-activated positron annihilation techniques are limited to use with materials that contain positron emitters (i.e., certain isotopes of copper, cobalt, and zinc).

SUMMARY OF THE INVENTION

A method for evaluating a material specimen comprises: Mounting a neutron source and a detector adjacent the material specimen; bombarding the material specimen with neutrons from the neutron source to create prompt gamma rays within the material specimen, some of the prompt gamma rays being emitted from the material specimen, some of the prompt gamma rays resulting in the formation of positrons within the material specimen by pair production; collecting positron annihilation data by detecting with the detector at least one emitted annihilation gamma ray resulting from the annihilation of a positron; storing the positron annihilation data on a data storage system for later retrieval and processing; and continuing to collect and store positron annihilation data, the continued collected and stored positron annihilation data being indicative of an accumulation of lattice damage over time.

BRIEF DESCRIPTION OF THE DRAWING

Illustrative and presently preferred embodiments of the invention are shown in the accompanying drawing in which.

DETAILED DESCRIPTION OF THE INVENTION

Figure 1:
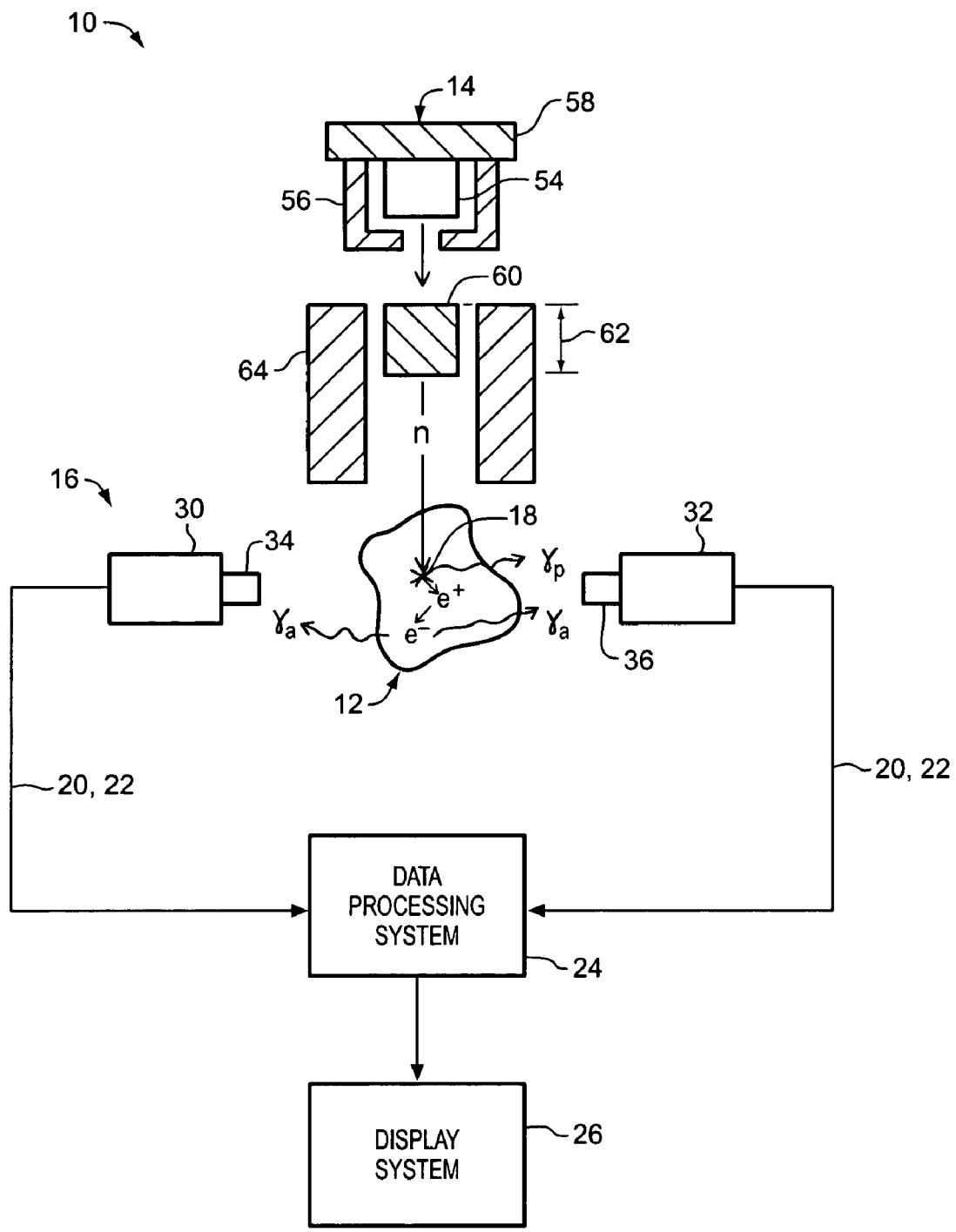
FIG. 1 is a schematic representation of apparatus for evaluating a material specimen according to one embodiment of the present invention.

One embodiment of apparatus 10 for evaluating a material specimen 12 is illustrated in FIG. 1 and may comprise a neutron source or generator 14 and a detector assembly 16. The neutron source or generator 14 produces neutrons n and directs the neutrons n toward the material specimen 12. The neutrons n interact with the material specimen 12, resulting in the production of prompt gamma rays $\gamma_p$. While some of the prompt gamma rays $\gamma_p$ are emitted from the material specimen 12, others of the prompt gamma rays $\gamma_p$ will result in the formation of positrons $e^+$ within the material specimen 12 through a process known as "pair production," (illustrated schematically in FIG. 1 at 18) More specifically, and as will be described in greater detail herein, prompt gamma rays $\gamma_p$ having energies greater than about 1.1 MeV are very likely to produce positrons $e^+$ within the material specimen 12. Many of the positrons $e^+$ produced as a result of the pair production process ultimately annihilate with electrons $e^-$ within the material specimen 12. The annihilation event results in the formation of annihilation gamma rays $\gamma_a$.

As mentioned above, some of the prompt gamma rays $\gamma_p$ resulting from the neutron bombardment of the material specimen 12 are emitted from the material specimen 12 and are detected by the detector assembly 16. In addition, some of the annihilation gamma rays $\gamma_a$ formed as a result of the annihilation of positrons $e^+$ and electrons $e^-$ are emitted from the material specimen 12 and are also detected by the detector assembly 16. The detector assembly 16 produces prompt gamma ray data 20 based on the detected prompt gamma rays $\gamma_p$ and positron annihilation data 22 based on the detected annihilation gamma rays $\gamma_a$. A data processing system 24 operatively associated with the detector assembly 16 processes the prompt gamma ray data 20 and the positron annihilation data 22 in accordance with certain algorithms (described below) in order to produce output data that are indicative of a lattice characteristic of the material specimen 12.

For example, in one embodiment, the data processing system 24 processes the prompt gamma ray data 20 and the positron annihilation data 22 in accordance with a positron lifetime algorithm 38 (FIG. 2) to produce positron lifetime data. Because the density of electrons is lower in defects contained in a material specimen compared to a defect-free material specimen, the mean lifetime of positrons trapped in defects is longer than those contained in a defect-free material. Further additional information on the sizes of the defects and other information, such as oxide inclusions, lattice structure variations, or localized composition changes, can be derived from the positron lifetime. Therefore, the positron lifetime data will be indicative of the presence of certain defects in the material specimen 12. Thereafter, the positron lifetime data and/or information relating to the presence of defects in the material specimen 12 may be presented in human-readable form on a suitable display system 26.

Figure 2:
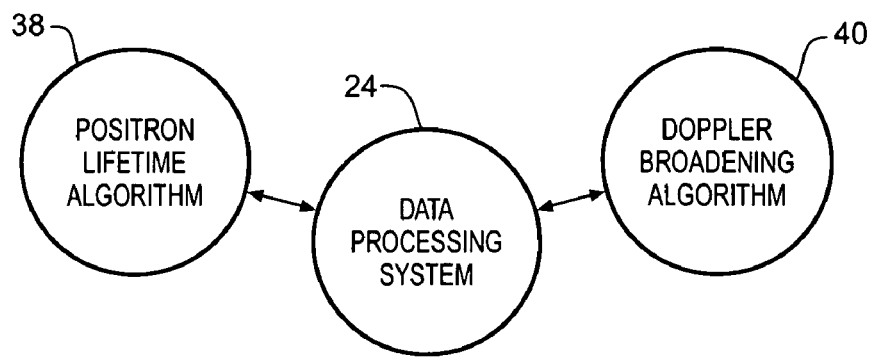
FIG. 2 is a schematic representation of the various algorithms that may be accessed by the data processing system.

The data processing system 24 may also be provided with a Doppler-broadening algorithm 40 (FIG. 2). The Doppler-broadening algorithm 40 is used to determine the degree of broadening of the gamma energy line (i.e., the 511 keV peak) of the detected annihilation gamma rays $\gamma_a$. The degree of broadening of the 511 keV peak is related to the momentum of the positron involved in the annihilation event. Therefore, the Doppler-broadening algorithm 40 may be used to assess certain characteristics associated with lattice defects contained in the material specimen 12, such as, for example, damage resulting from mechanical and thermal fatigue, embrittlement, annealing, or manufacturing defects. The resulting output data from the Doppler-broadening algorithm and/or information relating to certain lattice defects in the material specimen 12 may also be presented on the display system 26.

A significant advantage of the present invention relates to the ability to produce the positrons within the bulk of the material specimen itself, rather than externally and to produce positron lifetime or Doppler broadening spectral data using the prompt gamma ray produced from the interaction of neutrons within the material. As a result, the method and apparatus of the present invention may be used to evaluate the lattice characteristics contained within the bulk of the material specimen, rather than merely on the surface. Another advantage of the method and apparatus of the present invention is that it has increased sensitivity over conventional positron annihilation techniques that utilize external positron sources in that there is little extraneous background "noise" caused by annihilations external to the specimen being analyzed. The increased sensitivity also allows other types of detectors (e.g., germanium, $BaF_2$, or plastic) to be used. Moreover, the surface of the material specimen need not be specially prepared as is typically required with techniques that utilize external positron sources.

Still yet another advantage of the invention is that it may be used with any of a wide range of material specimens, as positron formation by the process of pair production does not require the material specimen to contain positron emitters, as is required if the positrons are to be formed via the process of neutron activation. Consequently, the present invention may be used in conjunction with a practically unlimited variety of material specimens.

Having briefly described one embodiment 10 of apparatus for evaluating a material specimen, as well as some of its more significant features and advantages, the various embodiments of methods and apparatus for evaluating a material specimen according to the present invention will now be described in detail.

With reference now specifically to FIG. 1, one embodiment of apparatus 10 for evaluating a material specimen 12 may comprise a neutron source 14 for directing neutrons n toward the material specimen 12. As discussed above, the neutrons n from the neutron source 14 interact with the material specimen 12 and result in the production of prompt gamma rays $\gamma_p$ within the material specimen 12. While some of the prompt gamma rays $\gamma_p$ are emitted from the material specimen 12, others of the prompt gamma rays $\gamma_p$ will result in the formation of positrons $e^+$ within the material specimen 12 through the process of pair production. Many of the positrons $e^+$ produced as a result of the pair production process ultimately annihilate with electrons $e^-$ within the material specimen 12. The annihilation event results in the formation of annihilation gamma rays $\gamma_a$, most of which are thereafter emitted from the material specimen 12.

Before proceeding, it should be noted that, in addition to the formation of positrons $e^+$ via the process of pair production, described above, positrons $e^+$ may also be formed within the material specimen 12 by a process known as "neutron activation" if the material specimen 12 contains a positron emitter (not shown) capable producing positrons $e^+$ in response to neutron bombardment. However, positron formation via the process of neutron activation is not of primary importance in the present invention and is not a significant component of the measurement response.

In accordance with the teachings contained herein, it is generally preferred that the neutrons n from the neutron source 14 have energies in the range of about 0.1 MeV to about 4 MeV. In accordance with this requirement, any of a wide range of neutron sources, such as neutron generators or isotopic neutron sources, may be used in conjunction with the present invention. Examples of neutron generators include, but are not limited to, deuterium-deuterium (D-D) and deuterium-tritium (D-T) generators of the type that are well-known in the art and readily commercially available. An example of an isotopic neutron source includes, but is not limited to, $^{252}Cf$.

In the embodiment shown in FIG. 1, the neutron source 14 comprises an isotopic neutron source 54, such as, for example $^{252}Cf$. The isotopic neutron source 54 may be surrounded by suitable shield 56 and reflector 58 to reduce stray neutron emission and to help direct additional neutrons n toward the material specimen 12. The shield 56 and reflector 58 may comprise any of a wide range of materials well-known in the art or that may be developed in the future that are or would be suitable for such uses, as would be obvious to persons having ordinary skill in the art after having become familiar with the teachings of the present invention. Consequently, the present invention should not be regarded as limited to a shield 56 and reflector 58 comprising any particular materials. However, by way of example, in one preferred embodiment, the shield 56 comprises lead, whereas the reflector 58 comprises carbon. In another embodiment, an additional reflector (not shown) may be positioned behind the material specimen 12 to direct neutrons n back toward the material specimen 12.

It is generally preferred, but not required, to provide a moderator or thermalizer 60 between the neutron source 14 and the material specimen 12. The thermalizer 60 thermalizes the neutrons n from the neutron source 14, reducing their energies, thereby improving the number of interactions within the material specimen 12. Accordingly, the amount of thermalization to be provided will depend on the energies of the neutrons n from the neutron source 14, as well as on certain characteristics (e.g., thickness, density, etc.) of the material specimen 12, being studied. Generally speaking, it is preferred that the prompt gamma rays $\gamma_p$ have energies of at least about 1.1 MeV, and preferably about 2.0 MeV, in order to produce high positron yields through the process of pair production. Because the energies of the prompt gamma rays $\gamma_p$ are not related to the energies of the bombarding neutrons n, variations in the neutron energies will result in the number of neutrons deposited in the material specimen 12 which must be controlled depending on the type of material specimen 12 being examined. Therefore, the thermalizer 60 should be configured to allow the specimen 12 to be bombarded with neutrons having the appropriate energies for the material specimen 12 and thickness being examined.

In one preferred embodiment, the thermalizer 60 comprises a material having a low atomic number, such as polyethylene. The overall length 62 of the polyethylene thermalizer 60 may be changed or varied as necessary to provide the desired degree of thermalization in accordance with the teachings provided herein. Alternatively, other types of thermalizers comprising other types of materials may be used, as would be obvious to persons having ordinary skill in the art after having become familiar with the teachings of the present invention.

It is generally preferred, but not required, to provide additional shielding 64 around the thermalizer 60 in order to further reduce the amount of radiation from the neutron source 14 that may reach the detector assembly 16. The presence of such additional shielding 64 will enhance the sensitivity of the detector assembly 16 by reducing the amount of "background" radiation or noise detected by the detector assembly 16. By way of example, in one preferred embodiment, such additional shielding 64 may comprise any of a wide range of bismuth, lead, or borated polymer materials.

The neutron source 14 is positioned adjacent the material specimen 12 to be tested so that neutrons n from the neutron source 14 are directed toward and bombard (i.e., penetrate) the portion of the material specimen 12 that is to be evaluated in accordance with the teachings of the present invention. In this regard it should be noted that any of a wide range of techniques may be used to irradiate the material specimen 12 with the neutrons n from the neutron source 14 so that the desired portions of the material specimen 12 are exposed to sufficient neutron flux to produce prompt gamma rays $\gamma_p$ having sufficient energies to produce a high flux of positrons $e^+$ through the process of pair production. Consequently, the present invention should not be regarded as limited to any particular technique for irradiating the material specimen 12.

However, by way of example, in one preferred embodiment, the material specimen 12 may be irradiated by moving the specimen 12 and neutron source 14 with respect to one another so that the desired region on the material specimen 12 is exposed to neutron flux from the neutron source in amounts sufficient to produce prompt gamma rays $\gamma_p$ having the desired energies, e.g., at least about 1.1 MeV and preferably about 2.0 MeV.

The detector assembly 16 may be positioned adjacent the material specimen 12 so that the detector assembly 16 receives both prompt gamma rays $\gamma_p$ and annihilation gamma rays $\gamma_a$ emitted from the specimen 12. In one embodiment, the detector assembly 16 comprises a first detector 30 and a second detector 32 positioned in generally opposed, spaced-apart relation in the manner illustrated in FIG. 1. As will be described in greater detail below, the detectors 30 and 32 comprising the detector assembly 16 may be used to detect prompt gamma rays $\gamma_p$ and/or annihilation gamma rays $\gamma_a$, depending on the particular algorithm (e.g., either the positron lifetime algorithm 38 or the Doppler broadening algorithm 40) that is being used to process the data. Therefore, it should be understood that the first detector 30 may produce prompt gamma ray data 20, positron annihilation data 22, or some combination of the two (if both prompt gamma rays $\gamma_p$ and annihilation gamma rays $\gamma_a$ are detected). Similarly, the second detector 32 may produce prompt gamma ray data 20, positron annihilation data 22, or some combination of the two.

The first detector 30 may be provided with a collimator 34, such as a variable slit or other type of collimator, to collimate the gamma rays (e.g., the prompt gamma rays $\gamma_p$ and/or the annihilation gamma rays $\gamma_a$, as the case may be) emitted by the material specimen 12. Similarly, the second detector 32 may be provided with a collimator 36 to collimate the gamma rays emitted by the material specimen 12. The collimator 36 may also comprise a variable slit collimator, although other types may be used.

It should be noted that the detectors 30 and 32 comprising the detector assembly 16 need not be positioned in opposed, spaced-apart relation in the manner schematically illustrated in FIG. 1. Instead, the detectors 30 and 32 may be located with respect to the material specimen 12 in any of a wide range of positions, as may be necessary or desirable in any particular circumstance and as would be obvious to persons having ordinary skill in the art after becoming familiar with the teachings provided herein.

Each detector 30 and 32 may comprise any of a wide range of detectors that are now known in the art or that may be developed in the future that are or would be suitable for detecting the prompt gamma rays $\gamma_p$ and the annihilation gamma rays $\gamma_a$. Consequently, the present invention should not be regarded as limited to any particular type of gamma ray detector. However, by way of example, in one preferred embodiment, each detector 30 and 32 may comprise a germanium detector of the type that is well-known in the art and readily commercially available. Alternatively, other types of detectors, such as $BaF_2$ or plastic-type detectors may be used.

The data processing system 24 is operatively associated with the detector system 16 and receives the prompt gamma ray data 20 and positron annihilation data 22 produced by the detector system 16. As was briefly described above, the data processing system 24 processes the prompt gamma ray data 20 and positron annihilation data 22 in accordance with a positron lifetime algorithm 38. See FIG. 2. So processing the prompt gamma ray data 20 and the positron annihilation data 22 results in positron lifetime data. In addition, the data processing system 24 may also process the positron annihilation data 22 in accordance with the Doppler-broadening algorithm 40.

The positron lifetime algorithm 38 is used to derive information regarding the characteristics of lattice defects contained in the material specimen 12. For example, the positron lifetime algorithm 38 may be used to obtain information as to whether the lattice defects comprise monovacancies, dislocations, slip zones, or particulate inclusions. In addition, information obtained from the mean lifetime of various defect components may be used to derive information relating to changing characteristics of the defects present in the specimen. The positron lifetime algorithm 38 basically involves a determination of an elapsed time between positron formation and positron annihilation. In order to do so, the positron lifetime algorithm utilizes the prompt gamma ray data 20 as well as the positron annihilation data 22. Because these data 20 and 22 are related to the prompt gamma ray $\gamma_p$ associated with the formation of the positron $e^+$, as well as the annihilation gamma rays $\gamma_a$ produced by the positron annihilation event, respectively, the time between these two events is the positron lifetime.

Figure 3:
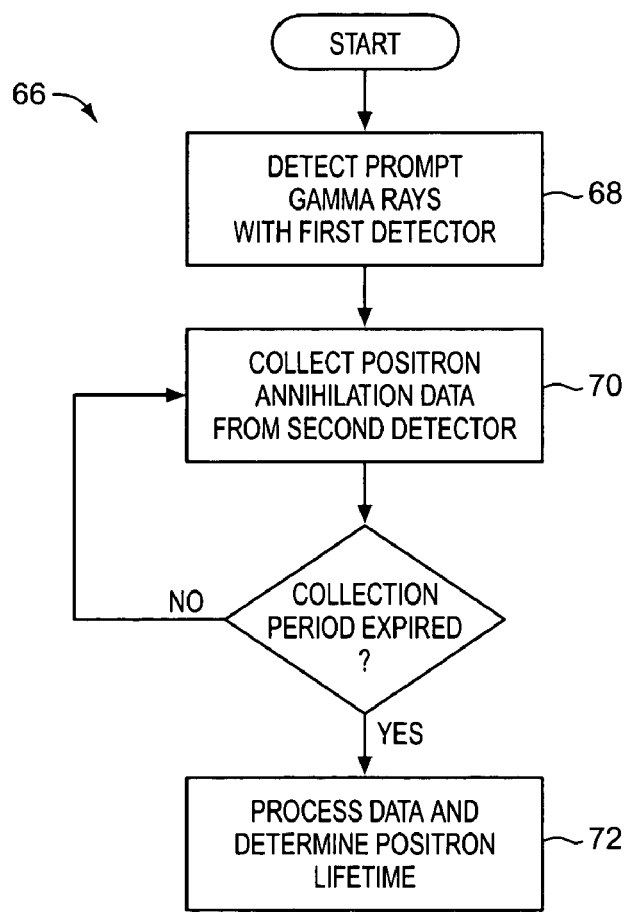
FIG. 3 is a flow diagram of one operational sequence for collecting data for the positron lifetime algorithm.

With reference now primarily to FIG. 3, the positron lifetime algorithm 38 may involve the use of both of the detectors 30 and 32 comprising the detector assembly 16 in order to determine positron lifetime. For example, in one operational sequence 66, the data processing system 24 monitors one of the detectors (e.g, detector 30) for prompt gamma ray data 20 at step 68. Upon detecting a prompt gamma ray $\gamma_p$, the data processing system 24 then monitors the other of the detectors (e.g., detector 32) and collects positron annihilation data 22 at step 70. The positron annihilation data 22 captured for a collection period that is between about 1 nanosecond (ns) to about 20 ns (12 ns preferred) after the detection of a prompt gamma ray $\gamma_p$ (step 68). Positron annihilation data 22 collected during the collection period corresponds to annihilation events resulting from the same events that caused the production of the prompt gamma ray. The data processing system 24 then processes the prompt gamma ray data and positron annihilation data in order to determine positron lifetime at step 72.

Figure 4:
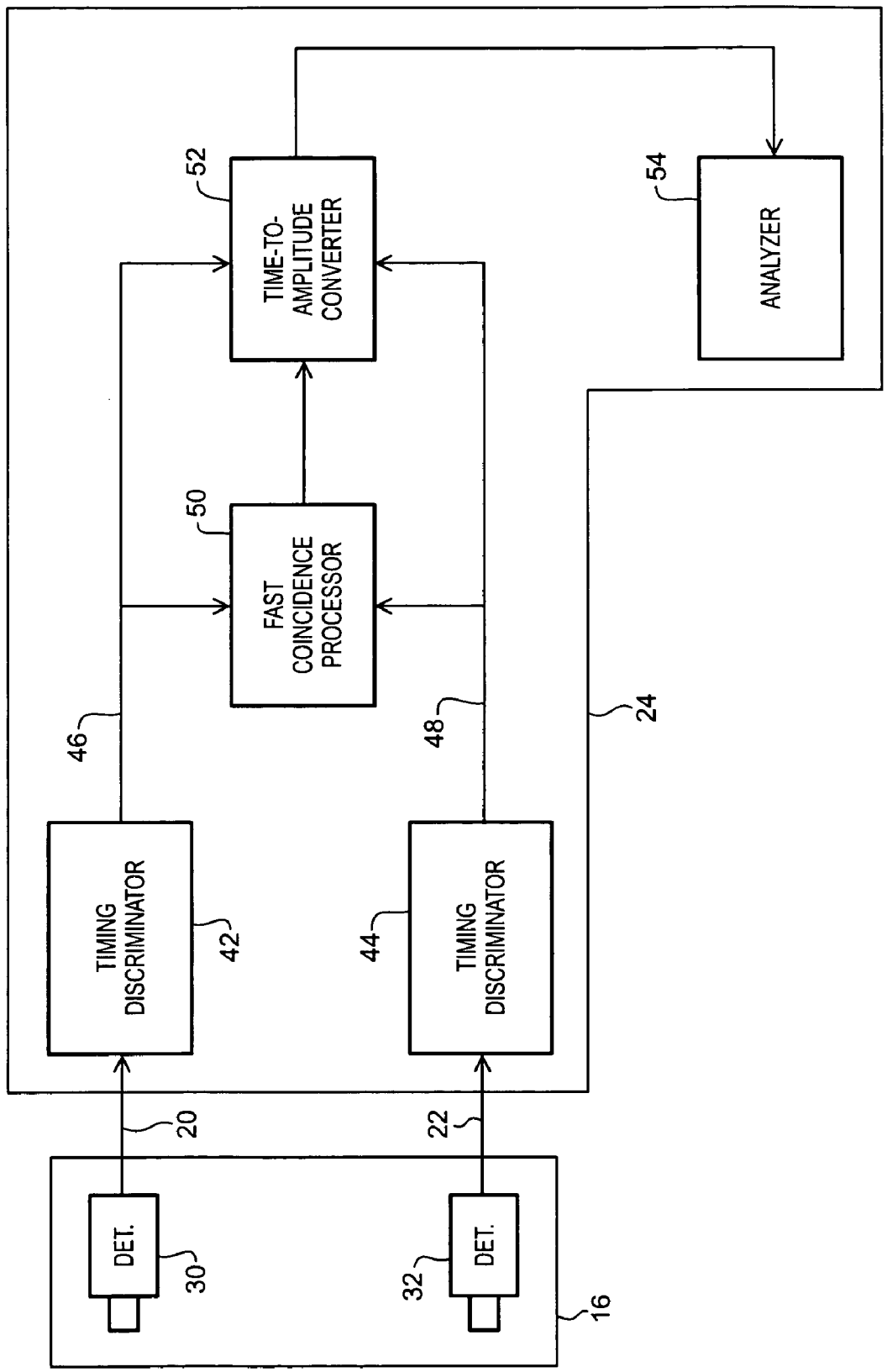
FIG. 4 is a block diagram of the data processing system illustrated in FIG. 1.

The operational sequence 66 may be achieved by providing the data processing system 24 with certain systems and devices illustrated in FIG. 4. More specifically, the data processing system 24 may be provided with a first timing discriminator 42 and a second timing discriminator 44. The first timing discriminator 42 is operatively connected to the first detector 30 of the detector assembly 16 and receives the prompt gamma ray data 20 produced by the first detector 30. The second timing discriminator 44 is operatively connected to the second detector 32 of the detector assembly 16 and receives positron annihilation data 22 from the second detector 32. The output 46 and 48 of each respective timing discriminator 42 and 44 is connected to a fast coincidence processor 50 and a time-to-amplitude converter 52 in the manner illustrated in FIG. 4. The combination of the timing discriminators 42 and 44, the fast coincidence processor 50, and the time-to-amplitude converter 52 allow the data processing system 24 to measure the time interval between the detection of the prompt gamma ray $\gamma_p$ and the annihilation gamma ray $\gamma_a$. From this time interval may be derived information regarding the average positron lifetime. This information may be further conditioned and/or processed, if required or desired, by an analyzer 54.

Alternatively, other arrangements are possible for determining positron lifetime. For example, in another embodiment, the data processing system 24 could be provided with a high-speed digital oscilloscope with recording capability. One channel of the oscilloscope is connected to the first detector 30, whereas the other channel of the oscilloscope is connected to the second detector 32. Data collected by each channel could then be correlated and analyzed in accordance with the teachings provided herein to determine positron lifetime. However, since systems for detecting positron lifetimes, as well as the algorithms utilized thereby, are well-known in the art and could be easily provided by persons having ordinary skill in the art after having become familiar with the details of the present invention, the positron lifetime algorithm 38, as well as the other systems and detector arrangements that may be required or desired, will not be described in further detail herein.

As was briefly mentioned above, the data processing system 24 may also utilize a Doppler-broadening algorithm 40. The Doppler-broadening algorithm 40 assesses the degree of broadening of the 511 keV peak associated with the annihilation gamma rays $\gamma_a$ produced by the positron/electron annihilation event. A broadening of the peak is indicative of the presence of one or more lattice defects in the material specimen 12. Such lattice defects may include, without limitation, damage resulting from mechanical and thermal fatigue, embrittlement, annealing, and manufacturing defects.

Figure 5:
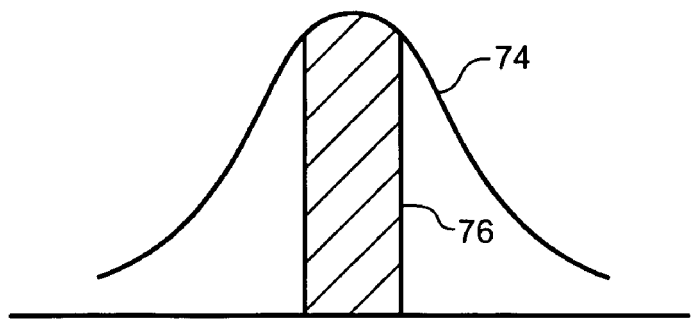
FIG. 5 is a graphical illustration of a 511 keV peak produced from collected positron annihilation data.

With reference now to FIG. 5, one method for determining the degree of broadening of the 511 keV peak 74 is based on a peak parameter, which may be defined as the number of counts in a central region 76 that contains about half of the total area of the 511 keV peak 74 divided by the total number of counts in the peak. Several different types of Doppler-broadening techniques have been developed and are being used in the positron annihilation art and could be easily implemented in the present invention by persons having ordinary skill in the art after having become familiar with the teachings of the present invention. Therefore, the present invention should not be regarded as limited to any particular Doppler-broadening algorithm. However, by way of example, in one preferred embodiment of the invention, the Doppler-broadening algorithm 40 may comprise the Doppler-broadening algorithm described in U.S. Pat. No. 6,178,218 B1, which is specifically incorporated herein by reference for all that it discloses.

Figure 6:
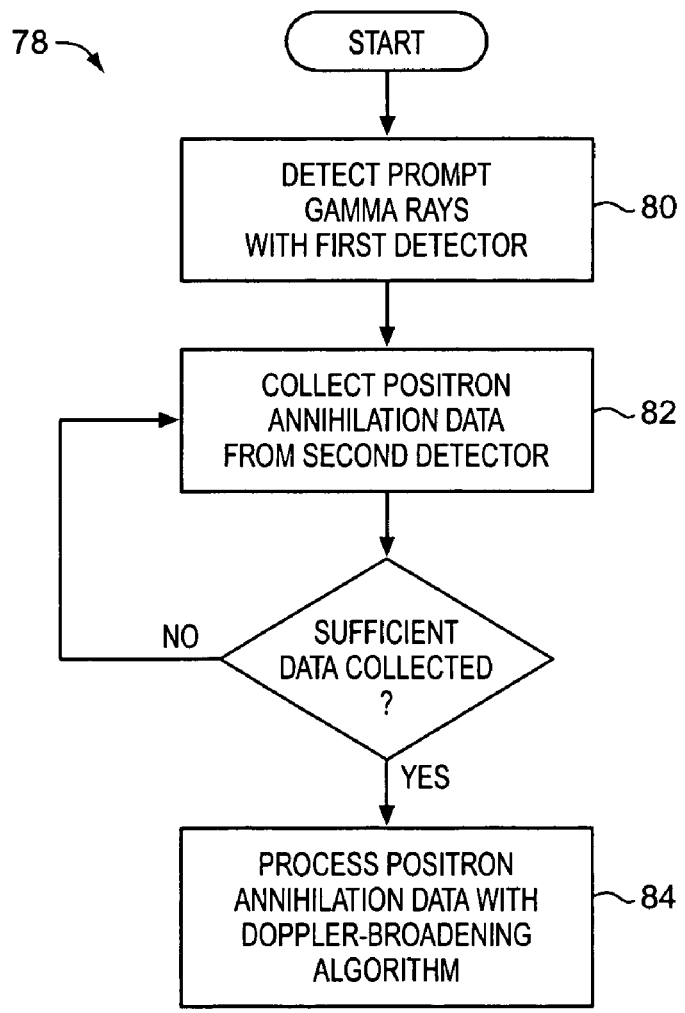
FIG. 6 is a flow diagram of one operational sequence for collecting data for the Doppler-broadening algorithm.

With reference now to FIG. 6, the Doppler-broadening algorithm 40 may also involve the use of both of the detectors 30 and 32 comprising the detector assembly 16 in order to determine the degree of broadening of the 511 keV peak 74. For example, in one operational sequence 78, the data processing system 24 monitors one of the detectors (e.g, detector 30) for prompt gamma ray data 20 at step 80. Upon detecting a prompt gamma ray $\gamma_p$, the data processing system 24 then monitors the other of the detectors (e.g., detector 32) and collects positron annihilation data 22 at step 82. After a sufficient amount of positron annihilation data 22 have been collected, the data processing system 24 processes the positron annihilation data 22 in accordance with the Doppler-broadening algorithm 40 at step 84. By way of example, in one preferred embodiment positron annihilation data 22 are collected for a period in the range of about 1-20 nanoseconds (12 nanoseconds preferred) after detecting the prompt gamma ray $\gamma_p$. This method significantly reduces background noise and increases the accuracy of the resulting data.

The apparatus 10 of the present invention may be used as follows in order to evaluate a material specimen. A first step in the process involves providing a material specimen 12. The next step of the process involves bombarding the material specimen 12 with neutrons n from the neutron source 14 in order to produce prompt gamma rays $\gamma_p$. This may be accomplished by positioning the material specimen 12 and neutron source 14 adjacent one another so that neutrons n from the neutron source 14 bombard the area or portion of the material specimen 12 that is to be evaluated. In this regard it should be noted that any of a wide range of neutron fluxes and exposure times may be required or desired depending on the particular material specimen 12 to be evaluated. Stated another way, the neutron flux and exposure to the neutron flux should be selected to result in the production of prompt gamma rays $\gamma_p$ having energies sufficient to produce a significant number of positrons $e^+$ through the process of pair production. As described herein, prompt gamma rays having energies of at least about 1.1 MeV and preferably about 2.0 MeV, are highly likely to produce positrons by pair production. Accordingly, the present invention should not be regarded as limited to any particular neutron flux or exposure time. However, by way of example, in one embodiment involving a material sample 12 comprising Alcoa 6061/T6 aluminum, a neutron source capable of producing from about $10^5$ to about $10^6$ neutrons per second for ten minutes has been observed to provide sufficient production of prompt gamma rays $\gamma_p$ and associated positron annihilation events.

Some of the prompt gamma rays $\gamma_p$ are emitted from the material specimen 12, whereas others of the prompt gamma rays $\gamma_p$ result in the production of positrons $e^+$ in the manner already described. Some of these positrons then annihilate with electrons contained in the material specimen 12, resulting in the production of annihilation gamma rays $\gamma_a$. The emitted prompt gamma rays $\gamma_p$ and annihilation gamma rays $\gamma_a$ are detected by the detectors 30 and 32. Positron lifetime data are then calculated based on the detected emitted prompt gamma rays $\gamma_p$ and the detected emitted annihilation gamma rays $\gamma_a$. The positron lifetime data may then be presented on the display system 26. If the data processing system 24 is provided with a Doppler-broadening algorithm 40, the detected emitted annihilation gamma rays $\gamma_a$ are used to produce output data indicative of a lattice characteristic of the material specimen 12. The output data from the Doppler-broadening algorithm 40 may also be presented on the display system 26.

Figure 7:
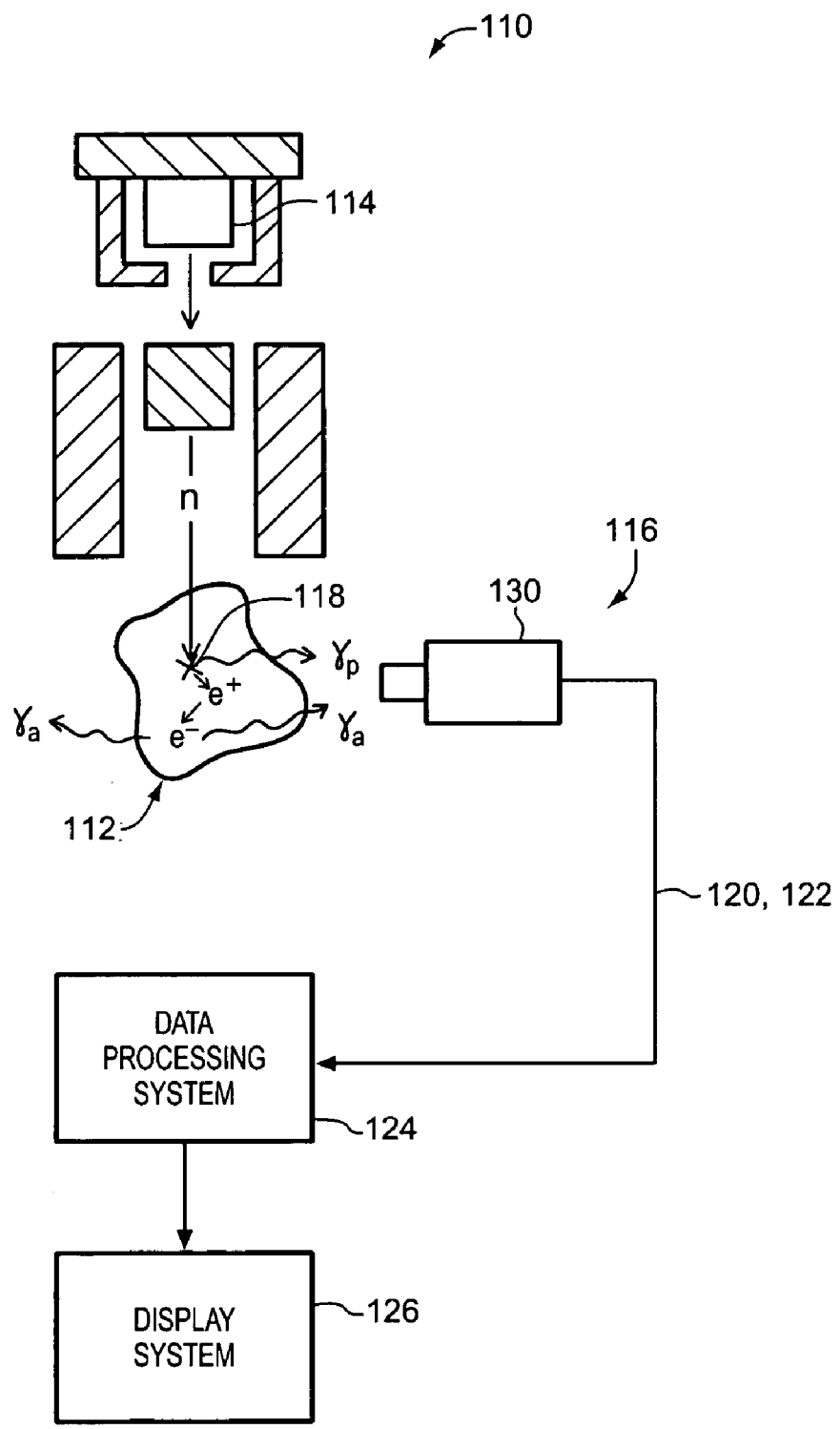
FIG. 7 is a schematic representation of apparatus for evaluating a material specimen according to another embodiment of the present invention.

A second embodiment 110 of apparatus for evaluating a material specimen 112 is illustrated in FIG. 7. This second embodiment 110 is similar to the first embodiment 10, in that it comprises a neutron source 114 and a detector assembly 116. However, the detector assembly 116 of the second embodiment 110 includes a single detector 130 for detecting both prompt gamma rays $\gamma_p$ and annihilation gamma rays $\gamma_a$. As was the case for the first embodiment 10, neutrons n from the neutron source 114 interact with the material specimen 112 to produce prompt gamma rays $\gamma_p$. Some of the prompt gamma rays $\gamma_p$ are emitted from the material specimen 112, while others result in the formation of positrons $e^+$ through the process of pair production, illustrated schematically at 118. Many of the positrons $e^+$ produced as a result of the pair production process ultimately annihilate with electrons $e^-$ in the material specimen 112, resulting in the formation of annihilation gamma rays $\gamma_a$.

The single detector 130 comprising the detector assembly 116 detects both prompt gamma rays $\gamma_p$ and annihilation gamma rays $\gamma_a$, and produces prompt gamma ray data 120 and positron annihilation data 122. A data processing system 124 operatively associated with the detector 130 processes the prompt gamma ray data 120 and positron annihilation data 122 in accordance with the methods already described for the first embodiment 10. Thereafter, positron lifetime data and/or information relating to the presence of defects in the material specimen 112 may be presented in human-readable form on a display system 126.

Because the data processing system 124 receives both prompt gamma ray data 120 and positron annihilation data 122 from the same detector 130 (as opposed to two different detectors 30 and 32 of the first embodiment 10), the data processing system 124 of the second embodiment 110 is also provided with list mode processing capability in order to process the data based on when it was received, as opposed to integrating the counts at each energy. However, since list mode data processing techniques are well-known in the art and could be easily provided by persons having ordinary skill in the art after having become familiar with the teachings of the present invention, the particular list mode processing technique utilized in the second embodiment 110 will not be described in further detail herein.

Figure 8:
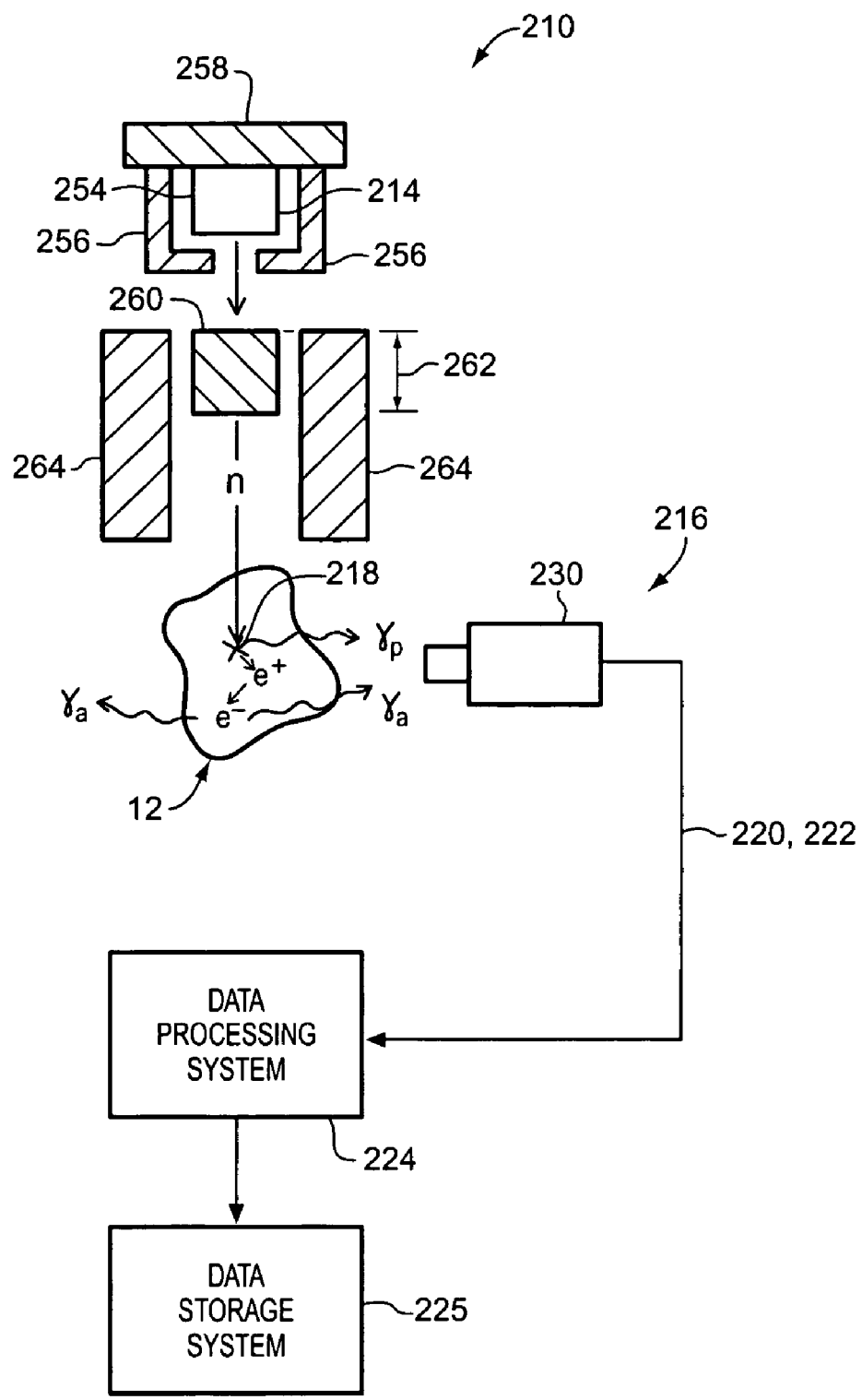
FIG. 8 is a schematic representation of a third embodiment of apparatus for evaluating a material specimen according to the present invention.

A third embodiment 210 of apparatus for evaluating a material specimen 212 is illustrated in FIG. 8 and may be used to measure the build-up or accumulation over time of lattice damage that may occur in the specimen 212 during fabrication and/or in-service use. This third embodiment 210 of apparatus for evaluating a material specimen 212 is referred to herein in the alternative as an "on-line sensor" or as apparatus for the "on-line" evaluation of the material specimen 212, in that it is intended to be used to evaluate the material specimen 212 over time.

Apparatus for the third embodiment 210 may be similar to either the apparatus for the first or second embodiments 10, 110 described above. That is, the third embodiment 210 may involve the use of two detectors (as is the case for the first embodiment 10) or a single detector (as is the case for the second embodiment 110). Consequently, the third embodiment 210 should not be regarded as being limited to the configuration of either the first embodiment 10 or the second embodiment 110. However, by way of example, as shown and described herein, the third embodiment 210 may comprise a neutron source 214 and a detector assembly 216 having a single detector 230. The neutron source 214 produces neutrons n and directs the neutrons n toward the material specimen 212. Alternatively the neutron source 214 could be replaced with a source of positrons (not shown) having energies of about 3 MeV if the material specimen to be examined is relatively thin.

As discussed above, the neutrons n from the neutron source 214 interact with the material specimen 212 and result in the production of prompt gamma rays $\gamma_p$ within the material specimen 212. While some of the prompt gamma rays $\gamma_p$ are emitted from the material specimen 212, others of the prompt gamma rays $\gamma_p$ will result in the formation of positrons $e^+$ within the material specimen 212 through the process of pair production (illustrated schematically at 218). Many of the positrons $e^+$ produced as a result of the pair production process ultimately annihilate with electrons $e^-$ within the material specimen 212. The annihilation event results in the formation of annihilation gamma rays $\gamma_a$, most of which are thereafter emitted from the material specimen 212.

As was the case for the first and second embodiments 10 and 110, it is generally preferred that the neutrons n from the neutron source 214 have energies in the range of about 0.1 MeV to about 4 MeV. In accordance with this requirement, any of a wide range of neutron sources, such as neutron generators or isotopic neutron sources, may be used in conjunction with the present invention. Examples of neutron generators include, but are not limited to, deuterium-deuterium (D-D) and deuterium-tritium (D-T) generators of the type that are well-known in the art and readily commercially available. An example of an isotopic neutron source includes, but is not limited to, $^{252}$Cf.

In the embodiment shown in FIG. 8, the neutron source 214 comprises an isotopic neutron source 254, such as, for example $^{252}$Cf. In order to accomplish the "on-line" evaluation of the material specimen 212 (e.g., the measurement over time of lattice characteristics of the material specimen 212), it is generally preferred that the neutron source 214 be mounted adjacent to or on the material specimen 212 in a long-term type of arrangement so that neutrons n from the neutron source 214 are directed toward and bombard (i.e., penetrate) the portion of the material specimen 212 that is to be evaluated.

For example, if the material specimen 212 to be evaluated comprises a portion of the structure of an aircraft (e.g., a wing spar), the neutron source 214 (e.g., the isotopic neutron source 254) may be mounted or affixed adjacent to the wing spar (i.e., the material specimen 212) to allow the neutron source 214 and detector 216 to be moved or scanned along the wing spar to identify changing conditions in the structure of the wing spar to continually bombard the spar with neutrons. Alternatively, the neutron source 214 may be mounted on the material specimen 212 (e.g., the wing spar) itself. Whether the neutron source 214 is mounted adjacent to or on the material specimen will depend on the configuration (e.g., size) of the material specimen as well as on the environment in which the measurement is to be taken, as would be obvious to persons having ordinary skill in the art after having become familiar with the teachings of the present invention. In addition, the mounting arrangement should be such that the desired portions of the spar (e.g., high stress areas) are exposed to sufficient neutron flux to produce prompt gamma rays $\gamma_p$ having sufficient energies to produce a high flux of positrons $e^+$ through the process of pair production in the manner already described herein. Generally speaking, this type of long-term mounting arrangement will be advantageous in a service environment, wherein it is desired to measure lattice damage as it builds-up during the service life, or some portion of the service life, of the material specimen 212. Alternatively, this type of long-term mounting arrangement may be used in other situations, as would be recognized by persons having ordinary skill in the art after having become familiar with the teachings of the present invention.

In an alternative arrangement, the neutron source 214 (e.g., the isotopic neutron source 254) could be temporarily placed adjacent to, or on, the material specimen 212 (e.g., a wing spar). Generally speaking, this type of temporary mounting arrangement will be advantageous in a production or fabrication environment, wherein it is desired to measure or monitor lattice damage as it may build-up or be created in the material specimen 212 (e.g., wing spar) during the production process. Alternatively, the temporary mounting arrangement may be used in other situations, as would be recognized by persons having ordinary skill in the art after having become familiar with the teachings of the present invention. As was the case for the other embodiments, any temporary mounting arrangement should be such that the desired portions of the material specimen 212 (e.g., wing spar under manufacture) are exposed to sufficient neutron flux to produce prompt gamma rays $\gamma_p$ having sufficient energies to produce a high flux of positrons $e^+$ through the process of pair production in the manner already described herein.

Depending on the particular situation in which the third embodiment 210 is utilized, it may be necessary or desirable to provide the neutron source 214 (e.g., the isotopic neutron source 254) with a suitable shield 256 and reflector 258 to reduce stray neutron emission and to help direct additional neutrons n toward the material specimen 212. As was the case for the other embodiments described herein, the shield 256 and reflector 258 may comprise any of a wide range of materials well-known in the art or that may be developed in the future that are or would be suitable for such uses, as would be obvious to persons having ordinary skill in the art after having become familiar with the teachings of the present invention. Consequently, the present invention should not be regarded as limited to a shield 256 and reflector 258 comprising any particular materials.

A moderator or thermalizer 260 may also be positioned between the neutron source 214 and the material specimen 212. The thermalizer 260 thermalizes the neutrons n from the neutron source 214, reducing their energies, thereby improving the number of interactions within the material specimen 212. As was described above, the amount of moderation or thermilization to be provided will depend on the energies of the neutrons n from the neutron source 214, as well as on certain characteristics (e.g., thickness, density, etc.) of the material specimen 212 being studied. Generally speaking, it is preferred that the prompt gamma rays $\gamma_p$ have energies of at least about 1.1 MeV, and preferably about 2.0 MeV, in order to produce high positron yields through the process of pair production.

In one preferred embodiment, the thermalizer 260 comprises a material having a low atomic number, such as polyethylene. The overall length 262 of the polyethylene thermalizer 260 may be changed or varied as necessary to provide the desired degree of moderation or thermalization in accordance with the teachings provided herein. Alternatively, other types of thermalizers comprising other types of materials may be used, as would be obvious to persons having ordinary skill in the art after having become familiar with the teachings of the present invention.

It is generally preferred, but not required, to provide additional shielding 264 around the thermalizer 260 in order to further reduce the amount of stray radiation from the neutron source 214 that may reach the detector assembly 216. The presence of such additional shielding 264 will enhance the sensitivity of the detector assembly 216 by reducing the amount of "background" radiation or noise detected by the detector assembly 216. By way of example, in one preferred embodiment, such additional shielding 264 may comprise any of a wide range of bismuth, lead, or borated polymer materials.

The detector assembly 216 may be positioned or mounted adjacent the material specimen 212 so that the detector assembly 216 receives both prompt gamma rays $\gamma_p$ and annihilation gamma rays $\gamma_a$ emitted from the specimen 212. Alternatively, the detector assembly 216 may be mounted to the material specimen 212, again depending on the particular material specimen 212 involved and the environment in which the measurement is to be performed.

In the embodiment shown in FIG. 8, the detector assembly 216 comprises a single detector 230 for detecting both prompt gamma rays $\gamma_p$ and annihilation gamma rays $\gamma_a$. As was described above for the second embodiment 110, the single detector 230 comprising the detector assembly 216 produces prompt gamma ray data 220 and positron annihilation data 222. A data processing system 224 operatively associated with the detector 230 processes the prompt gamma ray data 220 and the positron annihilation data 222 in accordance with the methods described herein. Thereafter, positron lifetime data and/or information relating to the build-up or accumulation of lattice defects may be captured or "downloaded" from the data processing system, as will be described in greater detail below.

As briefly mentioned above, in order to provide for the "on-line" evaluation capability, it is generally preferred that the detector assembly 216 be mounted adjacent to or even on the material specimen 212. Alternatively, the detector assembly 216 could be mounted so that it may be translated along the material specimen 212. The mounting arrangement may be either a long-term mounting system, or a temporary mounting system. In the long-term mounting system, the detector assembly 216 is mounted to (or nearby) the material specimen 212 in order to detect gamma rays over a relatively long term or period. Generally speaking, this type of long-term mounting arrangement will be advantageous in a service environment, wherein it is desired to measure lattice damage as it builds-up or accumulates during the service life, or some portion of the service life of the material specimen 212. Alternatively, this type of long-term mounting arrangement may be used in other situations, as would be recognized by persons having ordinary skill in the art after having become familiar with the teachings of the present invention.

In an alternative arrangement, the detector assembly 216 could be temporarily placed on (or nearby) the material specimen 212. Generally speaking, this type of temporary mounting arrangement will be advantageous in a production environment, wherein it is desired to measure or monitor lattice damage as it may build-up or be created in the material specimen 212 during the production or fabrication process. Alternatively, the temporary mounting arrangement may be used in other situations, as would be recognized by persons having ordinary skill in the art after having become familiar with the teachings of the present invention.

The data processing system 224 is operatively associated with the detector system 216 and receives the prompt gamma ray data 220 and positron annihilation data 222 produced by the detector system 216. As was briefly described above, the data processing system 224 may process the prompt gamma ray data 220 and positron annihilation data 222 in accordance with a positron lifetime algorithm (e.g., positron lifetime algorithm 38). So processing the prompt gamma ray data 220 and the positron annihilation data 222 results in positron lifetime data. In addition, the data processing system 224 may also process the positron annihilation data 222 in accordance with a Doppler-broadening algorithm (e.g., Doppler-broadening algorithm 40) in the manner already described for the first embodiment 10.

Alternatively, if the third embodiment 210 is to be used in a long-term arrangement, such as, for example, to measure the build-up or accumulation of lattice defects during the service life (or some portion of the service life) of the material specimen 212, the data processing system 224 could be simplified considerably to where the data processing system 224 serves merely as a data collection device, collecting the data (e.g., the prompt gamma ray data 220 and/or the positron annihilation data 222) produced by the detector assembly 216, and storing the data in a data storage system 225 for later retrieval and processing in accordance with the teachings provided herein. In such an application, the data storage system 225 could comprise any of a wide range of systems (e.g., magnetic or optical storage media) now known in the art or that may be developed in the future that are or would be suitable for storing such data for such time and under such conditions as may be required by the particular situation. Thereafter, the collected and stored data may be retrieved (i.e., downloaded) and processed in accordance with the teachings herein in order to provide information indicative of the build-up or accumulation of lattice defects during the data collection period.

Figure 9:
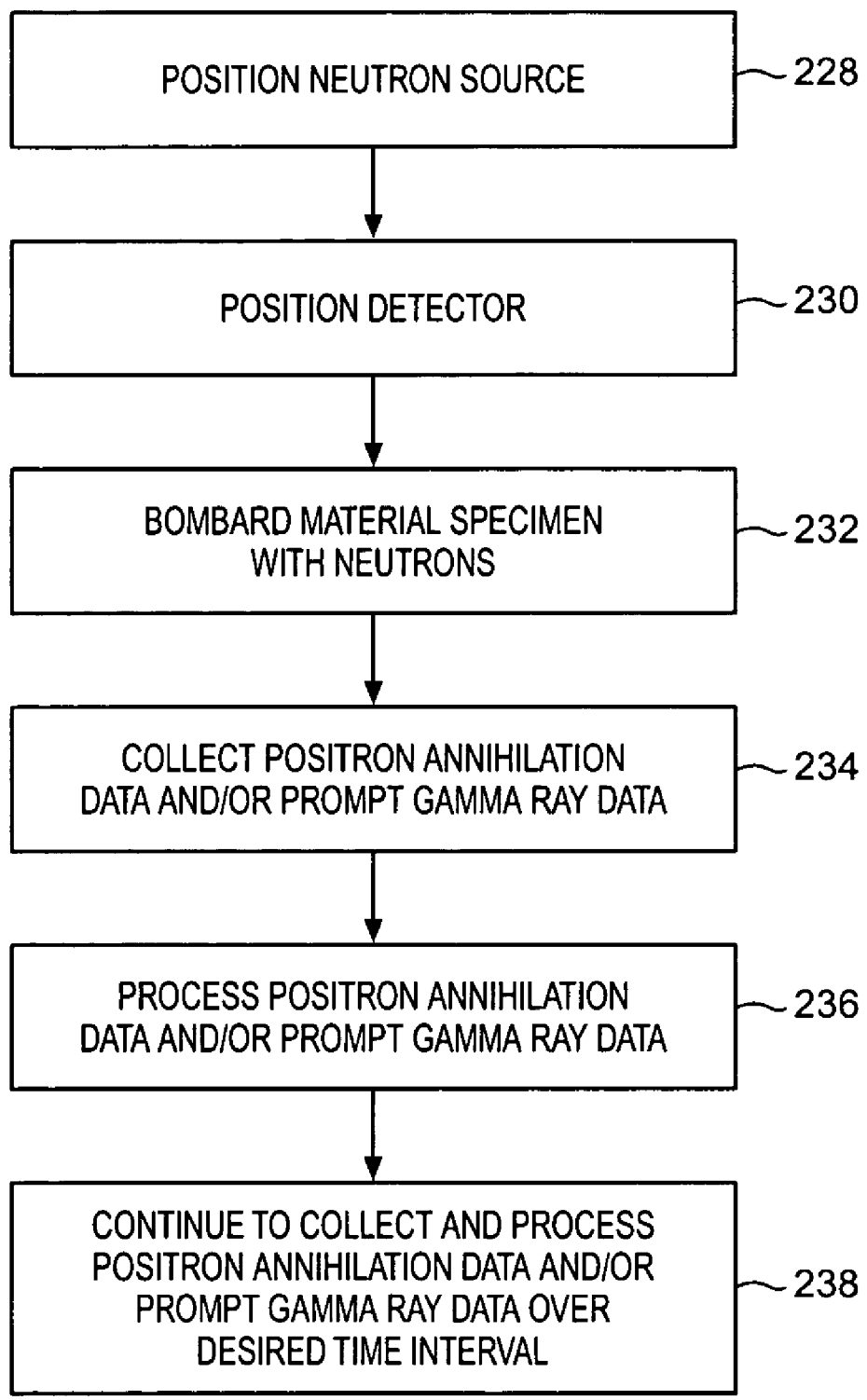
FIG. 9 is a flow diagram of a method for performing on-line evaluation of the material specimen.

The apparatus 210 of the present invention may be used in accordance with a method 226 illustrated in FIG. 9 to provide for the "on-line" evaluation of a material specimen. A first step 228 in the process involves positioning the neutron source 214 either adjacent to or actually on the material specimen 212. The detector assembly 216 may also be positioned either adjacent to or on the material specimen 212 at step 230. Of course, both the neutron source 214 and detector assembly 216 should be mounted so that neutrons from the neutron source 214 bombard the appropriate or desired portion or portions of the material specimen 212. Similarly, the detector assembly 216 should be mounted so that it will detect gamma rays (e.g., either prompt gamma rays or annihilation gamma rays, or both) emitted by the material specimen 212.

The next step 232 of method 226 involves bombarding the material specimen 212 with neutrons n from the neutron source 214 in order to produce prompt gamma rays $\gamma_p$. Again, this may be accomplished by mounting neutron source 214 to the material specimen 212 either in a long-term or a temporary arrangement so that neutrons n from the neutron source 214 bombard the area or portion of the material specimen 212 that is to be evaluated.

For example, if the third embodiment 210 is to be used in a long-term situation, such as, for example, to measure the build-up or accumulation of lattice defects during the service life, or some portion of the service life of the material specimen 212, then it will usually be desirable to mount the neutron source 214 on or nearby the specimen 212 so that the neutron source 214 will remain so during that portion of the service life of the specimen 212 that is desired to be monitored. The detector assembly 216 will also be mounted on or nearby the specimen 212 at the appropriate location so that the detector assembly 216 will remain so during the portion of the service life of the specimen 212 that is to be monitored.

The next step 234 involves collecting positron annihilation data and/or prompt gamma ray data from the detector assembly 216. The collected positron annihilation data 222 and/or prompt gamma ray data 220 are then processed by the data processing system 224 at step 236 in the manner already described. That is, the positron annihilation data 222 and/or prompt gamma ray data 220 may be processed in accordance with a Doppler-broadening algorithm (e.g., Doppler-broadening algorithm 40) and/or a positron lifetime algorithm (e.g., positron lifetime algorithm 38). The method 226 may then continue to collect and process the positron annihilation data 222 and/or prompt gamma ray data 220 at step 238 over the desired time interval. For example, the desired time interval may be some desired portion of the service life of the material specimen 212 or some desired portion of the production or fabrication sequence involving the material specimen 212.

While the data processing system 224 may immediately process the data from the detector assembly 216 in accordance with the description provided herein, the data processing system 224 may also be configured to collect the data storage system 225 the positron annihilation data 222 and/or prompt gamma ray data 220 and store the data on the data storage system 225 for later retrieval and processing.

If the third embodiment 210 is to be used in more of a temporary situation, such as, for example, to measure the build-up or accumulation of lattice defects in the material specimen 212 during a more short-term interval, such as during a production or fabrication process that involves the material specimen 212, then the neutron source 214 could be temporarily mounted on or nearby the specimen 212. The neutron source 214 may be left in place during the entire short-term monitoring process, during which time the detector assembly 216 provides prompt gamma ray data 220 and/or annihilation gamma ray data 222 to the data processing system 224. Alternatively, the neutron source 214 may be removed before collecting data from the detector assembly 216. Regardless of whether the neutron source is left in place or removed, the data processing system 224 may process the data 220 and 222 in the manner already described. For example, for monitoring continuous processes, a running average of the response will be processed so that larger pictures of the material specimen 212 can be monitored to assess changes in the material properties that can be fed back to the system controlling manufacture to provide an on-line quality assurance process. Positron lifetime data and/or data indicative of the build-up or accumulation of a lattice defect may then be presented on a suitable display device (e.g., display system 26, FIG. 1). Alternatively, the data may be collected and processed and/or displayed for the user at a later time.

It is contemplated that the inventive concepts herein described may be variously otherwise embodied and it is intended that the appended claims be construed to include alternative embodiments of the invention except insofar as limited by the prior art.

What is claimed is:

1. A method for evaluating a material specimen, comprising:
   mounting a neutron source adjacent the material specimen;
   mounting a detector adjacent the material specimen;
   bombarding the material specimen with neutrons from the neutron source to create prompt gamma rays within the material specimen, some of the prompt gamma rays being emitted from the material specimen, some of the prompt gamma rays resulting in the formation of positrons within the material specimen by pair production;
   collecting positron annihilation data by detecting with the detector a plurality of emitted annihilation gamma rays resulting from the annihilation of positrons, the detector producing the positron annihilation data;
   processing collected positron annihilation data in accordance with a Doppler-broadening algorithm; and
   continuing to collect and process positron annihilation data to measure an accumulation of lattice damage over time.

2. The method of claim 1, further comprising:
   collecting prompt gamma ray data by detecting with the detector a plurality of emitted prompt gamma rays, the detector producing the prompt gamma ray data;
   calculating positron lifetime data from the positron annihilation data and the prompt gamma ray data; and
   continuing to collect positron annihilation data and prompt gamma ray data and calculate positron lifetime data to measure an accumulation of lattice damage over time.

3. The method of claim 1, wherein said mounting a neutron source adjacent the material specimen comprises mounting the neutron source to the material specimen.

4. The method of claim 3, wherein said mounting a detector adjacent the material specimen comprises mounting the detector to the material specimen.

5. The method of claim 4, further comprising positioning a shield adjacent the neutron source to absorb stray neutrons.

6. The method of claim 5, further comprising positioning a moderator between the neutron source and the material specimen.

7. The method of claim 6, further comprising positioning a reflector adjacent the neutron source to reflect neutrons toward the material specimen.

8. The method of claim 1, wherein mounting a neutron source adjacent the material specimen comprises mounting an isotopic neutron source adjacent the material specimen.

9. The method of claim 8, wherein mounting an isotopic neutron source adjacent the material specimen comprises mounting a neutron source of $^{252}$Cf.

10. The method of claim 1, wherein continuing to collect and process positron annihilation data to measure an accumulation of lattice damage over time is performed while the material specimen is in service.

11. A method for evaluating a material specimen, comprising:
mounting a neutron source adjacent the material specimen;
mounting a detector adjacent the material specimen;
bombarding the material specimen with neutrons from the neutron source to create prompt gamma rays within the material specimen, some of the prompt gamma rays being emitted from the material specimen, some of the prompt gamma rays resulting in the formation of positrons within the material specimen by pair production;
collecting positron annihilation data by detecting with the detector a plurality of emitted annihilation gamma rays resulting from the annihilation of positrons, the detector producing the positron annihilation data;
storing the positron annihilation data on a data storage system for later retrieval and processing; and
continuing to collect and store positron annihilation data, the continued collected and stored positron annihilation data being indicative of an accumulation of lattice damage over time.

12. The method of claim 11, further comprising:
collecting prompt gamma ray data by detecting with the detector a plurality of emitted prompt gamma rays, the detector producing the prompt gamma ray data; storing prompt gamma ray data on the data storage system for later retrieval and processing; and continuing to collect and store prompt gamma ray data, the continued collected and stored prompt gamma ray data being indicative of an accumulation of lattice damage over time.

13. The method of claim 11, wherein said mounting a neutron source adjacent the material specimen comprises mounting the neutron source to the material specimen.

14. The method of claim 13, wherein said mounting a detector adjacent the material specimen comprises mounting the detector to the material specimen.

15. The method of claim 14, further comprising positioning a shield adjacent the neutron source to absorb stray neutrons.

16. The method of claim 15, further comprising positioning a moderator between the neutron source and the material specimen.

17. The method of claim 11, wherein mounting a neutron source adjacent the material specimen comprises mounting an isotopic neutron source adjacent the material specimen.

18. The method of claim 11, wherein continuing to collect and store positron annihilation data is performed while the material specimen is in service.

19. The method of claim 11, further comprising: retrieving stored positron annihilation data; and
processing the positron annihilation data in accordance with a Doppler-broadening algorithm to produce output data indicative of an accumulation of lattice damage over time.

20. The method of claim 1, further comprising removing the neutron source before collecting positron annihilation data.

21. The method of claim 11, further comprising removing the neutron source before collecting positron annihilation data.

* * * * *